United States Patent
Jiao et al.

(10) Patent No.: US 9,795,543 B1
(45) Date of Patent: Oct. 24, 2017

(54) NANO-COMPLEXES FOR ENAMEL REMINERALIZATION

(71) Applicant: Pac-Dent International Inc., Brea, CA (US)

(72) Inventors: Susan Jiao, Irvine, CA (US); Daniel Wang, Brea, CA (US); Bo Tao, Chino, CA (US); Xiao Yang, La Habra, CA (US)

(73) Assignee: PAC-DENT INTERNATIONAL INC., Brea, CA (US)

( * ) Notice: Subject to any disclaimer, the term of this patent is extended or adjusted under 35 U.S.C. 154(b) by 0 days.

(21) Appl. No.: 15/400,301

(22) Filed: Jan. 6, 2017

(51) Int. Cl.
| | |
|---|---|
| *A61K 8/86* | (2006.01) |
| *A61K 8/02* | (2006.01) |
| *A61Q 11/00* | (2006.01) |
| *A61K 8/24* | (2006.01) |
| *A61K 8/81* | (2006.01) |
| *A61K 8/73* | (2006.01) |
| *C08J 3/12* | (2006.01) |
| *C08J 3/14* | (2006.01) |

(52) U.S. Cl.
CPC ............ *A61K 8/0291* (2013.01); *A61K 8/022* (2013.01); *A61K 8/24* (2013.01); *A61K 8/736* (2013.01); *A61K 8/8164* (2013.01); *A61K 8/86* (2013.01); *A61Q 11/00* (2013.01); *C08J 3/12* (2013.01); *C08J 3/14* (2013.01); *A61K 2800/48* (2013.01); *A61K 2800/524* (2013.01); *A61K 2800/5424* (2013.01); *A61K 2800/5426* (2013.01); *C08J 2305/08* (2013.01); *C08J 2325/08* (2013.01); *C08J 2335/00* (2013.01); *C08J 2371/02* (2013.01)

(58) Field of Classification Search
CPC .................................................. A61K 31/203
USPC ........................................................ 423/305
See application file for complete search history.

(56) References Cited

U.S. PATENT DOCUMENTS

| | | | | |
|---|---|---|---|---|
| 5,650,176 | A * | 7/1997 | Lee ............................ | A61F 2/28 423/308 |
| 7,390,526 | B2 * | 6/2008 | Stupp ....................... | A61L 27/32 427/2.26 |
| 2006/0257306 | A1 * | 11/2006 | Yamamoto ............ | C01B 25/327 423/305 |
| 2006/0270752 | A1 * | 11/2006 | Xu ........................... | A61L 27/44 523/116 |
| 2007/0178220 | A1 * | 8/2007 | Karlinsey ................. | A61K 8/24 427/2.1 |
| 2007/0264481 | A1 * | 11/2007 | DeSimone ............ | A61K 9/5138 428/220 |
| 2008/0077222 | A1 * | 3/2008 | Johnson ................ | A61L 31/005 623/1.2 |
| 2010/0311902 | A1 * | 12/2010 | Yamamoto ............... | C01B 25/32 525/54.1 |
| 2014/0255502 | A1 * | 9/2014 | Chen ..................... | A61K 9/5115 424/492 |

FOREIGN PATENT DOCUMENTS

EP             1674093       *    6/2006    ........... A61K 31/203

* cited by examiner

*Primary Examiner* — Walter Webb

(57) ABSTRACT

The invention relates to nano-sized complexes formed by associating amorphous calcium phosphate (ACP) and/or amorphous calcium fluoride phosphate (ACFP) with an amphiphilic polymer surfactant. The amphiphilic polymer surfactants can form nano-sized assemblies in aqueous solution, serving as a nano dispersant preventing ACP and/or ACFP from aggregation, and as a nano carrier associating or attaching ACP and/or ACFP, stabilizing ACP and/or ACFP against the conversion to a crystalline form as well, thus maintaining calcium and phosphate/and fluoride ions in a bioavailable state for dental re-mineralization and prevention of dental caries, dental calculus and dental hypersensitivity. A method for the nano-sized complex preparation and compositions comprising the nano-sized complexes are also provided.

20 Claims, 2 Drawing Sheets

Schematic representation of the complex structure showing
a. APS micelle structure and surface arrangement
b. APS stabilized ACP/ACFP nano complex structure.

NANO-COMPLEXES FOR ENAMEL REMINERALIZATION

BACKGROUND OF THE INVENTION

Field of the Invention

This invention relates to nano-sized complexes formed by associating or attaching amorphous calcium phosphate (ACP) and/or amorphous calcium fluoride phosphate (ACFP) with an amphiphilic polymeric surfactant (APS). In particular, the amphiphilic polymeric surfactants (APSs) form nano-sized assemblies in micellar structure that consists of a hydrophobic core surrounded by a shell of hydrophilic blocks in aqueous solution, serving as a nano-dispersant, preventing ACP and/or ACFP from aggregating, and as a nano-carrier associating or attaching ACP and/or ACFP and stabilizing ACP and/or ACFP against the conversion to a crystalline form as well. The nano-complexes may be used in oral care for enamel re-mineralization. Methods for preparing the ACP/ACFP stabilized nano-sized complexes and compositions comprising the nano-sized complexes are also provided in the present disclosure.

Background Information

Re-mineralization and demineralization are dynamic processes occurring in the oral environment. The ratio between re-mineralization and demineralization determines the hardness and strength of the tooth structure. White spot lesions and cavities result when the rate of demineralization exceeds the rate of re-mineralization, typically in a process that requires many months or years. Re-mineralization of tooth enamel is the process whereby calcium and phosphate ions are supplied from a source external to the tooth structure to restore mineral ions in demineralized enamel. A range of calcium-phosphate-based re-mineralization systems has been developed for clinical use. One technology is bioactive glass containing calcium sodium phosphosilicate (NOVAMIN™), the second is an un-stabilized amorphous calcium phosphate (ACP, ENAMELON™), and the third involves casein phosphopeptide stabilized amorphous calcium phosphate (CPP-ACP; RECALDENT™).

U.S. Pat. Nos. 5,745,942 and 6,086,374 (each of which is incorporated by reference herein, in its entirety) disclose a novel silica based bioactive glass composition that can be used in conjunction with a delivery agent such as a toothpaste, gel, and the like, having a particle size range <90 μm which will form a rapid and continuous reaction with body fluids due to the immediate and long term ionic release of Ca and P from the core silica particles, to produce a stable crystalline hydroxy carbonate apatite layer deposited onto and into the dentin tubules for the immediate and long term reduction of dentin hypersensitivity and tooth surface re-mineralization. U.S. Pat. No. 8,741,269 (incorporated by reference herein, in its entirety) discloses non-aqueous dentifrice compositions containing a bioacceptable and bioactive glass with improved mouth-feel, foam, and product stability. U.S. Pat. No. 8,715,625 (incorporated by reference herein, in its entirety) discloses a natural anhydrous oral care composition with a limited number of naturally-derived, naturally processed, generally regarded as safe (GRAS) ingredients including an effective amount of a bioactive glass. The topical application of the composition to human teeth cleanses, re-mineralizes and reduces plaque build-up on teeth. A commercial bioactive glass that has been used in the treatment of dental hypersensitivity and enamel re-mineralization is NOVAMIN®, a material which was originally developed as a bone regeneration material.

Amorphous calcium phosphate (ACP) compound is an ideal source of calcium phosphate ions because of its high solubility. The Amorphous Calcium Phosphate (ACP) technology is an un-stabilized calcium and phosphate system that has been developed and commercialized. U.S. Pat. No. 5,427,768 (incorporated by reference herein, in its entirety) discloses calcium phosphate solutions which are supersaturated with respect to calcium phosphate solids and carbon dioxide. The solutions deposit calcium phosphate compounds with or without fluoride on and in the tooth weaknesses such as dental caries, exposed root, or dentin. U.S. Pat. Nos. 5,037,639 and 5,268,167 (each of which is incorporated by reference herein, in its entirety) disclosed the use of amorphous calcium compound such as amorphous calcium phosphate (ACP), amorphous calcium phosphate fluoride (ACFP), and amorphous calcium carbonate phosphate (ACCP) for mineralizing and fluoridating calcified tissues. Amorphous calcium phosphate (ACP) was incorporated into Arm & Hammer's Enamel Care Toothpaste, Discus Dental's Nite White bleaching gel and Premier Dental's Enamel Pro Polishing paste. To keep the calcium ions and phosphate ions from reacting with each other before use, the above products were delivered though a dual-compartment system or delivered in a product with a low water activity.

However, the ACP compounds are unstable when in contact with saliva in the oral environment and transform rapidly into a stable, crystalline form, which has low solubility and thus poor bioavailability. Insoluble calcium phosphates are not easily applied, do not localize effectively at the tooth surface and require acid for solubility to produce ions capable of diffusing into enamel subsurface lesions. On the other hand, soluble calcium and phosphate ions can only be used at very low concentrations due to the intrinsic insolubility of the calcium phosphates, in particular the calcium fluoride phosphates. Soluble calcium and phosphate ions do not substantially incorporate into dental plaque or localize at the tooth surface to produce effective concentration gradients to drive diffusion into the subsurface enamel. The clinical use of calcium and phosphate ions for re-mineralization has not been successful in the past and the efficacy of re-mineralization of the ACP/ACFP remains in doubt because ACP/ACFP transforms to a poorly soluble phase in saliva, and in doing so, may act to promote dental calculus. Several approaches have been developed recently to enhance re-mineralization of ACP/ACFP in tooth enamel.

Casein is the major protein group found in bovine milk and accounts for almost 80% of the total protein. Casein phosphopeptides (CPP) obtained through tryptic digestion have been shown to stabilize amorphous calcium phosphate (ACP) and amorphous calcium fluoride phosphate (ACFP) by binding calcium on the surfaces of the calcium and phosphate ions clusters and hence preventing growth of the calcium and phosphate ion clusters to the critical size for nucleation and phase transformation. The CPP stabilized ACP complex (CPP-ACP) and CPP stabilized ACFP complex (CPP-ACFP) were patented by Reynolds et al. in U.S. Pat. Nos. 6,780,844, 7,312,193, 8,609,071 (each of which is incorporated by reference herein, in its entirety), and the like. Numerous scientific evidences have demonstrated that CPP-CPP and CPP-ACFP can promote the re-mineralization of enamel subsurface lesions and prevent demineralization, as the complexes provide a bioavailable source of calcium and phosphate ions at a high concentration, penetrating into the tooth enamel. In addition, the complexes bind to the surface of dental calculus and prevent or reduce further accretion. These complexes have been incorporated into commercial sugar-free chewing gum (Trident Xtra Care), Recaldent and dental cream (Tooth Mousse and Tooth Mousse Plus, MI Paste and MI Paste Plus). However, the use of CPP-ACP/CPP-ACFP is limited because of milk protein allergy caused by casein.

The objective of the present invention is to provide nano-sized complexes formed by associating amorphous calcium phosphate (ACP) and/or amorphous calcium fluoride phosphate (ACFP) with an amphiphilic polymeric surfactant (APS). These novel nano-complexes are free of potential milk protein allergy due to the use of amphiphilic polymeric surfactant as a nano-carrier of ACP. In aqueous solution, the amphiphilic polymeric surfactants (APSs) form nano-sized assemblies in micellar structure that consists of hydrophobic core surrounded by a shell of hydrophilic blocks. The APS micelles serve as a nano-dispersant preventing ACP and/or ACFP from aggregating and as a nano-carrier improving the attachment or association of the polymer and ACP and/or ACFP and thus stabilizing ACP and/or ACFP against transforming to a crystalline form as well. The nano-complexes may be used in oral care for tooth re-mineralization.

Methods for preparing the nano-sized complexes and composition comprising the nano-sized complexes are provided in the present invention.

SUMMARY OF THE INVENTION

The present invention provides a nano-sized complex, where the complex is formed by associating ACP or ACFP with an amphiphilic polymeric surfactant (APS). The APS micelles may serve as a nano-dispersant preventing the ACP and/or ACFP from aggregation, as well as a nano-carrier associating the ACP and/or ACFP with APS molecules, where the micelles stabilize the ACP/ACFP against conversion to crystalline apatite, and thus, re-mineralization of enamel via ACP/ACFP may be enhanced. Methods for preparing the APS stabilized ACP/ACFP nano-sized complexes and compositions thereof are also provided in the present invention. The nano-sized complexes and the compositions may be used in oral care for tooth re-mineralization.

In embodiments, a nano-sized micellar complex is disclosed containing an amorphous phosphate (AP) including amorphous calcium phosphate (ACP), an amorphous calcium fluoride phosphate (ACFP) or a combination thereof, and an amphiphilic polymer surfactant (APS).

In one aspect, the ratio of the APS to the AP is between about 5:95 to about 95:5 in weight. In another aspect, the APS includes di-block polyethylene oxide and polypropylene oxide (PEO-PPO) copolymer; di-block polyethylene oxide and poly(butylene oxide) (PEO-PBO) copolymer; tri-block PEO-PPO-PEO copolymer; tri-block PEO-PBO-PEO copolymer, polyalkylene co-acrylic acid; polyalkylene co-maleic anhydride; polyalkylene co-polyacrylic acid; polyalkylene co-maleic acid; polyalkylene sulfonic acid co-maleic acid; and polystyrene co-acrylic acid; polystyrene co-maleic anhydride; polystyrene co-polyacrylic acid; polystyrene co-maleic acid; polystyrene sulfonic acid co maleic acid; polyalkylene polyamine; polystyrene polyamine; cationic polyamine and combinations thereof.

In a related aspect, the APS includes both hydrophilic chains and hydrophilic blocks, where the nano-sized micellar complex exhibits a structure having hydrophobic core surrounded by a shell of hydrophilic blocks in aqueous solution.

In a further related aspect, the APS has molecular weight ranging from about 500 to about 500,000 kDa.

In another aspect, the complex is less than about 100 nm.

In embodiments, a method for preparing a nano-sized micellar complex containing an amorphous phosphate (AP) selected from amorphous calcium phosphate (ACP), an amorphous calcium fluoride phosphate (ACFP) or a combination thereof, and an amphiphilic polymer surfactant (APS) is disclosed including dissolving the APS in aqueous solution and adjusting the pH of the resulting aqueous solution to about 5-10; adding calcium or fluoride ions and phosphate ions to the pH adjusted APS containing aqueous solution under stirring, and thereby forming nano-sized complexes; collecting the nano-sized complexes by ultrafiltration; optionally (a) washing with said collected nano-sized complexes with a hydroalcoholic solution or (b) dialysing said nano-sized complexes against DI water; and freeze-drying or spray drying the nano-sized complex to form a powder.

In a related aspect, the pH of APS solution is adjusted by the addition of an acid or base including hydrochloric acid, phosphoric acid, nitric acid, citric acid, maleic acid, sodium hydroxide, potassium hydroxide or ammonium hydroxide.

In one aspect, the ions are added as salt solutions. In another aspect, the calcium ions are added by a solution including dissolved calcium chloride, calcium nitrate or combinations thereof. In a related aspect, the calcium salt solution further contains about 0.1% to 2% (w/w) of polymeric surfactant including polyethylene glycol, polyvinyl alcohol, polyvinylpyrrolidone, or combinations thereof.

In another aspect, the phosphate ions are added by a solution including dissolved diammonium hydrogen phosphate, disodium hydrogen phosphate, dipotassium hydrogen phosphate, or combinations thereof.

In one aspect, the fluoride ions are added by a solution including dissolved ammonium fluoride, sodium fluoride or combinations thereof.

In another aspect, the calcium containing salt solution and the phosphate salt containing solution are added simultaneously to the pH adjusted APS solution.

In embodiments, a kit is disclosed including a nano-sized micellar complex containing an amorphous phosphate (AP) selected from amorphous calcium phosphate (ACP), an amorphous calcium fluoride phosphate (ACFP) or a combination thereof, and an amphiphilic polymer surfactant (APS); a container; a label; and instructions on use of the complex.

In another embodiment, a composition is disclosed containing an APS stabilized amorphous calcium phosphate (ACP) or an APS stabilized amorphous calcium fluoride phosphate (ACFP) nano-sized micellar complex, where the micellar complex composition re-mineralizes enamel.

In one aspect, the composition includes about 0.1% to 30% by weight of nano-complex.

In another aspect, the composition includes a powder, gel, paste or suspension.

In one aspect, the composition further includes one or more thickeners, humectants, surfactants, preservatives or combinations thereof.

In embodiments, a method of treating a subject in need thereof is disclosed, including administering a composition containing an APS stabilized amorphous calcium phosphate (ACP) or an APS stabilized amorphous calcium fluoride phosphate (ACFP) nano-sized micellar complex, where the micellar complex composition re-mineralizes tooth enamel.

DETAILED DESCRIPTION OF THE INVENTION

Figure 1:
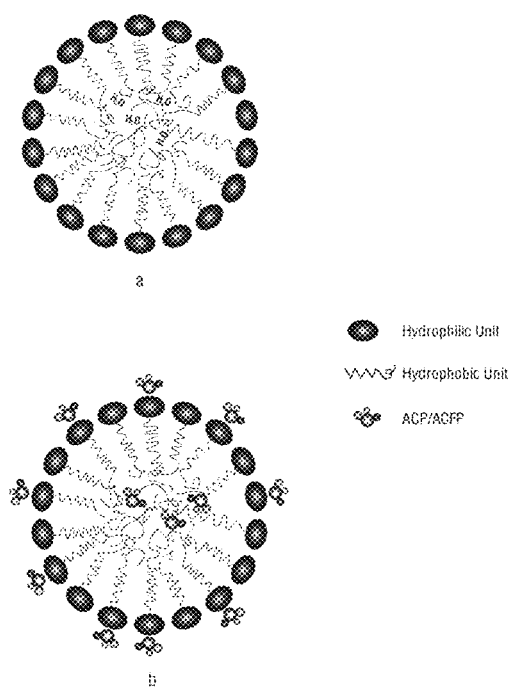
FIG. 1 shows the schematic representation of the complex structure showing (a) APS micelle structure and surface arrangement and (b) nano-complex structure

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

As used herein, "about," "approximately," "substantially" and "significantly" will be understood by a person of ordinary skill in the art and will vary in some extent depending on the context in which they are used. If there are uses of the term which are not clear to persons of ordinary skill in the art given the context in which it is used, "about" and "approximately" will mean plus or minus <10% of particular term and "substantially" and "significantly" will mean plus or minus >10% of the particular term. In embodiments, composition may "contain", "comprise" or "consist essentially of" a particular component of group of components, where the skilled artisan would understand the latter to mean the scope of the claim is limited to the specified materials or steps "and those that do not materially affect the basic and novel characteristic(s)" of the claimed invention.

The nano-sized complexes of the present invention are composed of amorphous calcium phosphate (ACP) and/or amorphous calcium fluoride phosphate (ACFP) associated or complexed with amphiphilic polymer surfactant (APS). By association or complexation with the amphiphilic polymer, ACP and/or ACFP can be stabilized against the conversion to crystalline apatite and thus enamel re-mineralization of ACP and/or ACFP may be enhanced.

"Amphiphilic polymers" refer to molecules that both attract and repel water. The amphiphilic polymer surfactants (APS) are composed of hydrophilic (water-loving) and hydrophobic (water-hating) parts. As amphiphilic polymers reduce surface tension and are used as surfactants, "amphiphilic polymer" and "amphiphilic polymer surfactant" are interchangeably used in the present invention.

Based on colloid chemistry, when amphiphilic polymer surfactants (APS) consist of both hydrophilic chains and hydrophobic blocks with appropriate lengths, APS molecules may form nano-sized assemblies in a micellar structure (FIG. 1) in aqueous solution. The micelles may be composed of a central core of dense hydrophobic units and an outer shell of hydrophilic units. To a good approximation, the micelles are spherical objects with a diameter less than 100 nm. Due to its capability of forming micelles, the amphiphilic polymer serves as a nano-dispersant, preventing ACP/ACFP from aggregation to big particles, solubilizing (or increasing the solubility of) ACP/ACFP. Meanwhile, the hydrophilic shell of micelles interacts or associates with hydrophilic amorphous calcium phosphate (ACP) and/or ACFP, improving the attachment or association of ACP and/or ACFP molecules with the amphiphilic polymer as an anchor, because of the numerous contact points mediated by hydrophobic interaction and crosslinking of the polymer shell. By association or attaching ACP and/or ACFP molecules with the amphiphilic polymer, which serves as a nano-carrier, ACP and/or ACFP are further stabilized against the conversion to crystalline apatite, and thus enamel re-mineralization can be enhanced. FIG. 1 b shows the schematic representation of the structure of APS stabilized ACP/ACFP nano-sized complex. Based on the above-mentioned mechanism, a desirable requirement on the dispersant is the ability to stabilize ACP and/or ACFP against aggregation to large particles and transforming to the crystalline form.

Amphiphilic polymers meet the above-mentioned requirement. In one aspect, the APS of the present invention forms nano-sized assembly micelles due to consisting of both hydrophilic chains and hydrophobic blocks. Moreover, the amphiphilic polymer surfactant (APS) can prevent ACP and/or ACFP from aggregation to large particles and stabilize ACP and/or ACFP against transforming to the stable crystalline form as the APS micelles disperse ACP/ACFP and improve the attachment or association of ACP and/or ACFP molecules with the polymer (APS).

In another aspect, the APSs are selected from the group of non-ionic polymer surfactants and ionic polymer surfactants and the mixture thereof. The non-ionic polymer surfactants include (but not limited to) di-block polyethylene oxide and polypropylene oxide (PEO-PPO) copolymer (with PPO as hydrophobic blocks and PEO as hydrophilic blocks); di-block polyethylene oxide and poly (butylene oxide) (PEO-PBO) copolymer (with PBO as hydrophobic blocks and PEO as hydrophilic blocks); tri-block PEO-PPO-PEO copolymer; tri-block PEO-PBO-PEO copolymer and the like. The ionic polymer surfactants include (but not limited to) polyalkylene co acrylic acid; polyalkylene co maleic anhydride; polyalkylene co polyacrylic acid; polyalkylene co maleic acid; polyalkylene sulfonic acid co maleic acid; and polystyrene co acrylic acid; polystyrene co maleic anhydride; polystyrene co polyacrylic acid; polystyrene co maleic acid; polystyrene sulfonic acid co maleic acid. The ionic surfactants may also be polycationic polymers, such as polyalkylene polyamine; polystyrene polyamine, the copolymers consisting of cationic polyamine, chitosan and its derivatives, and the like.

As mentioned above, the formation of micelles in aqueous solution gives surfactants ability to disperse and stabilize ACP/ACFP. The micelle formation is controlled by the pattern of the polymer molecules, the molecular weight and ratio of hydrophilic units to hydrophobic units. In the present invention, in one aspect, the APS contain both hydrophilic chains and hydrophobic blocks with appropriate lengths, enabling APS molecules to form nano-sized assembly in micellar structure that consists of hydrophobic core surrounded by a shell of hydrophilic blocks in aqueous solution.

In another aspect, the APS have molecular weight ranging from 500 to 500,000 kDa.

In the present invention, the APS stabilized ACP/ACFP nano-sized complex was prepared as follows: i) dissolving the APS in aqueous solution and adjusting pH to 5-9; ii) adding calcium ions and phosphate/and fluoride ions under stirring; iii) collecting the nano-sized complex by ultrafiltration and washing with deionized water and alcohol after re-dispersion or dialysis in deionized water; iv) obtaining the complex powder by freeze-drying or spray-drying. In one aspect, the washing may be done at least one time, two times or three times.

In colloidal and surface chemistry, the critical micelle concentration (CMC) is defined as the concentration above which micelles form. At low surfactant concentration the surfactant molecules arrange on the surface. When more surfactant is added the surface tension of the solution starts to rapidly decrease since more and more surfactant molecules will be on the surface. When the surface becomes saturated, the addition of the surfactant molecules will lead to formation of micelles. This concentration point is called critical micelle concentration. CMC of a certain amphiphilic polymer may be affected by temperature, pH values, addition of salts or nonelectrolytes, and the like.

According to the invention, the APS may be dissolved in aqueous solution and adjusted pH to 5-9 by the addition of acids or bases, including but not limited to, hydrochloric acid; phosphoric acid; nitric acid, citric acid, maleic acid, and the like; sodium hydroxide, potassium hydroxide or ammonium hydroxide, and the like.

According to the invention, calcium ions and phosphate/and fluoride ions may be present in the calcium containing solution (salt), phosphate containing/and fluoride containing solution (salt).

Optionally, calcium containing solution may contain about 0.1% to 2% polymeric surfactants, such as polyethylene glycol, polyvinyl alcohol, polyvinylpyrrolidone, and the like, to solubilize calcium ions.

According to the invention, the calcium ion may be selected from the group consisting of calcium chloride, calcium nitrate solution (salt), and the like; and the phosphate containing solution may be selected from the group consisting of diammonium hydrogen phosphate solution, disodium hydrogen phosphate solution and dipotassium hydrogen phosphate solution, and the like, and the fluoride containing solution may be selected from the group consisting of ammonium fluoride, sodium fluoride, and the like.

According to the invention, calcium containing solution and the phosphate containing solution and/or fluoride containing solution may be added simultaneously to the APS solution under vigorous stirring.

In a further aspect, the present invention provides a dental care composition comprising the APS stabilized ACP/ACFP nano-sized complex (nano-complex for abbreviation). In embodiments, the dental composition may comprise about 0.1 to 30% of nano-complex by weight. In embodiments, the dental composition of the present invention may contain about 2% APS-ACP, APS-ACFP or a mixture of both. The dental composition of the present invention may be prepared and used in various forms such as tooth powder, cream or gel, toothpaste, prophy paste, chewable tablets, chewing gum, or mouthwash, denture products, mouth sprays, dental patch, or strip and etc. The dental composition according to this invention may further include additional ingredients such as thickeners, humectants, surfactants, antibacterial agents, preservatives, flavorants, sweeteners, colorants, and the like, depending on the type and form of a particular oral composition.

The following examples will further describe the present invention without, however, at the same time, constituting any limitation thereof.

Examples

Example 1. Preparation of the Nano-Complex with a Non-Ionic Amphiphilic Polymer, Polyethylene Oxide and Polypropylene Oxide (PEO-PPO) Copolymer The ACP nano-complex was prepared as follows: 0.4 M $CaCl_2$-PEG solution was prepared by dissolving 4.44 g $CaCl_2$ and 0.4 g PEG 8000 in 100 mL deionized (DI) water. 0.5 M phosphate solution was prepared by dissolving 8.71 g $K_2HPO_4$ in 100 mL DI water; 10% (w/w) of polyethylene oxide and polypropylene oxide (PEO-PPO) copolymer (PPO-PEO) solution was prepared by dissolving 10 g of polymer in 90 mL DI water. 3.6 mL of 0.4 M $CaCl_2$-PEG solution and 6.0 mL of 0.5 M $K_2HPO_4$ solution were added drop-wise into 10 mL of 10% (w/w) PPO-PEO solution under vigorous stirring for 30 min. The reaction temperature was kept at 0~4° C. in ice-water bath. The nano-complex was cleaned (to remove the extra free calcium ions or phosphate ions) by dialysis in DI water for at least 48 hours. The nano-complex powder was obtained by freeze-drying.

Figure 2:
FIG. 2 shows a photograph of suspensions of Examples: (a) Example 1; (b) Example 2; (c) Example 3; and (d) Example 4.

0.2 g of the obtained nano-complex powder were dispersed in 10 mL DI water and a picture of this solution was shown in FIG. 2 a. The concentration of the soluble calcium and total calcium were detected respectively, and listed in Table 1.

TABLE 1

| | Calcium concentration (% w/w) in the powder examples | |
|---|---|---|
| Example | Soluble Calcium % w/w | Total Calcium % w/w |
| 1 | 1.5 | 6.5 |
| 2 | 3.9 | 5.7 |
| 3 | 1.8 | 10.6 |
| 4 | ~0 | 34.5 |

Example 2. Preparation of the Nano-Complex with Anionic Amphiphilic Polymer, Copolymer of Styrene-Maleic Acid The ACP nano-complex was prepared as follows: Instead of polyethylene oxide and polypropylene oxide (PEO-PPO) copolymer of Example 1, 10 g of sodium solution of copolymer of styrene-co-maleic acid (Na-SMA) was neutralized to pH 9.0 by adding hydrochloric acid. 3.6 mL of 0.4 M $CaCl_2$-PEG solution and 6.0 mL of 0.5 M $K_2HPO_4$ solution were added drop-wise into the SMA solution under vigorous stirring for 30 min. The reaction temperature was kept at room temperature. The extra free calcium ions or phosphate ions were removed by dialysis in DI water for at least 48 hours. The nano-complex powder was obtained by freeze-drying.

0.2 g of the obtained nano-complex powder were dispersed in 10 mL DI water and a picture of this solution was shown in FIG. 2 b. The concentrations of the soluble calcium and total calcium were detected respectively, and listed in Table 1.

Example 3. Preparation of the Nano-Complex with Cationic Amphiphilic Polymer, Chitosan The ACP nano complex was prepared as follows: Instead of polyethylene oxide and polypropylene oxide (PEO-PPO) copolymer of Example 1, 2.5 g of chitosan was dissolved in 97.5 of hydrochloride acid-DI water solution (pH was adjusted to 5.0). 3.6 mL of 0.4 M $CaCl_2$-PEG solution and 6.0 mL of 0.5 M $K_2HPO_4$ solution were added drop-wise into the chitosan solution under vigorous stirring for 30 min. The reaction temperature was kept at room temperature. The extra free calcium ions or phosphate ions were removed by dialysis in DI water for at least 48 hours. The nano-complex powder was obtained by freeze-drying.

0.2 g of the obtained nano-complex powder were dispersed in 10 mL DI water and a picture of this solution was shown in FIG. 2 c. The concentrations of the soluble calcium and total calcium were detected respectively, and listed in Table 1.

For comparison, calcium phosphate was prepared by adding 3.6 mL of 0.4 M $CaCl_2$-PEG solution and 6.0 mL of 0.5 M $K_2HPO_4$ solution dropwise into 10 g of DI water under vigorous stirring for 30 min. The reaction temperature was kept at room temperature. The precipitate was collected by ultrafiltration and washed with DI water and alcohol after re-dispersion, respectively. The nano-complex powder was obtained by freeze-drying. The picture of the precipitated calcium phosphate was shown in FIG. 2 d. The concentrations of the soluble calcium and total calcium were detected respectively, and listed in Table 1.

Example 4. Preparation of the Nano-Complex with Cationic Amphiphilic Polymer, PEG As shown in FIG. 2, the suspensions of nano complex prepared with the nonionic amphiphilic polymer, anionic amphiphilic polymer and cationic amphiphilic polymer, respectively (Example 1, 2, and 3) are colloidal and milky, but the suspension of calcium phosphate is not.

As shown in Table 1, the concentrations of soluble calcium in Example 1, 2, and 3 are higher than that in Example 4, indicating the addition of the amphiphilic polymer enhances solubility of calcium phosphate or stabilizes ACP/ACFP against the conversion to non-soluble form as calcium phosphate in Example 4.

Example 5. Toothpaste Formulation Containing APS-ACP

In Example 5, a formulation is provided for making toothpaste containing APS-ACP nano-complex (Table 2).

TABLE 2

| Toothpaste formulation containing APS-ACP | |
|---|---|
| Ingredient | % w/w |
| Sorbitol | 25.0 |
| Glycerin | 31.75 |
| Sodium Fluoride | 0.25 |
| Sodium Saccharin | 0.3 |
| Sodium Carboxymethyl Cellulose | 0.5 |
| Sodium Pyrophosphate | 2.0 |

TABLE 2-continued

| Toothpaste formulation containing APS-ACP | |
|---|---|
| Ingredient | % w/w |
| Sodium Benzoate | 0.2 |
| Purified Water 10 | 10.0 |
| Hydrated Silica | 25 |
| APS (anionic polymer)-ACP | 2.0 |
| Sodium Lauryl Sulfate | 2.0 |
| Flavorant | 1.0 |

Example 6. Prophypaste Formulation Containing APS-ACP

In Example 6, a formulation is provided for making prophypaste containing APS-ACP nano-complex (Table 3).

TABLE 3

| Prophypaste formulation containing APS-ACP | |
|---|---|
| Ingredient | % w/w |
| Purified Water | 8.0 |
| Glycerin | 19.2 |
| Sodium Fluoride | 2.72 |
| Sodium Saccharin | 0.4 |
| Sodium Carboxymethyl Cellulose | 0.1 |
| Sodium Pyrophosphate | 2.0 |
| Sodium Benzoate | 0.2 |
| Chlorhexidine | 0.38 |
| Hydrated Silica | 2.0 |
| APS (anionic polymer)-ACP | 2.0 |
| Sodium Citrate | 2.0 |
| Flavorant | 1.0 |
| Pumice | 60.0 |

Example 7. Re-Mineralization Gel Formulation Containing APS-ACP

In Example 7, a formulation is provided for making re-mineralization gel containing APS-ACP nano complex (Table 4).

TABLE 4

| Re-mineralization gel formulation containing APS-ACP | |
|---|---|
| Ingredient | % w/w |
| Purified Water | 50.0 |
| Glycerin | 29.25 |
| Sodium Fluoride | 0.55 |
| Sodium Saccharin | 0.5 |
| Polyacrylic Acid | 4.0 |
| Manganese Gluconate | 1.0 |
| Sodium Pyrophosphate | 1.5 |
| Sodium Benzoate | 0.2 |
| APS (anionic polymer)-ACP | 4.0 |
| Potassium Nitrate | 5.0 |
| Flavorant | 1.0 |
| Polyvinylpyrrolidone | 2.0 |
| Potassium Hydroxide (50% w/w solution) | 1.0 |

Example 8. Mouthwash Formulation Containing APS-ACP

In Example 8, a formulation is provided for making mouthwash containing APS-ACP nano-complex (Table 5).

TABLE 5

Mouthwash formulation containing APS-ACP

| Ingredient | % w/w |
|---|---|
| Purified Water | 84.6 |
| Ethanol | 10 |
| Sodium Saccharin | 0.2 |
| Sodium Pyrophosphate | 0.3 |
| Sodium Benzoate | 0.2 |
| APS (anionic polymer)-ACP | 1.0 |
| Chlorhexidine | 0.2 |
| Flavorant | 1.0 |
| Zinc Chloride | 2.0 |
| Lauryl Diethanolannide | 0.5 |

It is understandable that the above compositions or formulations are only examples of the type of formulations. The invention disclosed and defined extends to all alternative combinations of two or more of the individual features mentioned or evident from the text or drawings. All of the combinations constitute various alternative aspects of the invention.

We claim herein:

1. A nano-sized micellar complex comprising an amorphous phosphate (AP) selected from amorphous calcium phosphate (ACP), an amorphous calcium fluoride phosphate (ACFP) or a combination thereof, and an amphiphilic polymer surfactant (APS).

2. The nano-sized micellar complex of claim 1, wherein the ratio of the APS to the AP is between about 5:95 to about 95:5 in weight.

3. The nano-sized micellar complex of claim 1, wherein the APS is selected from the group consisting of di-block polyethylene oxide and polypropylene oxide (PEO-PPO) copolymer; di-block polyethylene oxide and poly(butylene oxide) (PEO-PBO) copolymer; tri-block PEO-PPO-PEO copolymer; tri-block PEO-PBO-PEO copolymer, polyalkylene co-acrylic acid; polyalkylene co-maleic anhydride; polyalkylene co-polyacrylic acid; polyalkylene co-maleic acid; polyalkylene sulfonic acid co-maleic acid; and polystyrene co-acrylic acid; polystyrene co-maleic anhydride; polystyrene co-polyacrylic acid; polystyrene co-maleic acid; polystyrene sulfonic acid co maleic acid; polyalkylene polyamine; polystyrene polyamine; cationic polyamine and combinations thereof.

4. The nano-sized micellar complex of claim 3, wherein APS comprises both hydrophilic chains and hydrophobic blocks, and wherein said nano-sized micellar complex exhibits a structure having hydrophobic core surrounded by a shell of hydrophilic blocks in aqueous solution.

5. The nano-sized micellar complex of claim 3, wherein the APS has molecular weight ranging from about 500 to about 500,000 kDa.

6. The nano-sized micellar complex of claim 1, wherein the complex is less than about 100 nm.

7. A method for preparing a nano-sized micellar complex containing an amorphous phosphate (AP) selected from amorphous calcium phosphate (ACP), an amorphous calcium fluoride phosphate (ACFP) or a combination thereof, and an amphiphilic polymer surfactant (APS) comprising:
   i) dissolving the APS in aqueous solution and adjusting the pH of the resulting aqueous solution to about 5-10;
   ii) adding (a1) calcium or fluoride ions and (b1) phosphate ions to the pH adjusted APS containing aqueous solution under stirring, and thereby forming nano-sized complexes;
   iii) collecting the nano-sized complexes by ultrafiltration;
   iv) optionally
      (a2) washing with said collected nano-sized complexes with a hydroalcoholic solution or
      (b2) dialysing said nano-sized complexes against DI water; and
   v) freeze-drying or spray drying the nano-sized complex to form a powder.

8. The method of claim 7, wherein the pH of APS solution is adjusted by the addition of an acid or base selected from the group consisting of hydrochloric acid, phosphoric acid, nitric acid, citric acid, maleic acid, sodium hydroxide, potassium hydroxide or ammonium hydroxide.

9. The method of claim 7, wherein the ions are added as salt solutions.

10. The method of claim 7, wherein the calcium ions are added by a solution comprising dissolved calcium chloride, calcium nitrate or combinations thereof.

11. The method of claim 9, wherein the calcium salt solution further comprises about 0.1% to 2% (w/w) of polymeric surfactant selected from polyethylene glycol, polyvinyl alcohol, polyvinylpyrrolidone, or combinations thereof.

12. The method of claim 9, wherein the phosphate ions are added by a solution comprising dissolved diammonium hydrogen phosphate, disodium hydrogen phosphate, dipotassium hydrogen phosphate, or combinations thereof.

13. The method of claim 9, wherein the fluoride ions are added by a solution comprising dissolved ammonium fluoride, sodium fluoride or combinations thereof.

14. The method of claim 9, wherein the calcium containing salt solution and the phosphate salt containing solution are added simultaneously to the pH adjusted APS solution.

15. A kit comprising:
   a. a nano-sized micellar complex comprising an amorphous phosphate (AP) selected from amorphous calcium phosphate (ACP), an amorphous calcium fluoride phosphate (ACFP) or a combination thereof, and an amphiphilic polymer surfactant (APS);
   b. a container;
   c. a label; and
   d. instructions on use of the complex.

16. A composition comprising an amphiphilic polymer surfactant (APS) stabilized amorphous calcium phosphate (ACP) or an APS stabilized amorphous calcium fluoride phosphate (ACFP) nano-sized micellar complex, wherein said micellar complex re-mineralizes tooth enamel.

17. The nano-sized complex composition of claim 16, wherein said composition comprises about 0.1% to 30% by weight of nano-complex.

18. The nano complex composition of claim 14, wherein said composition is selected from a powder, gel, paste or suspension.

19. The nano complex composition of claim 14, wherein said composition further comprises one or more thickeners, humectants, surfactants, preservatives or combinations thereof.

20. A method of treating a subject in need thereof, comprising administering the composition of claim 16.

* * * * *